United States Patent
Kaneda et al.

(10) Patent No.: US 12,187,691 B2
(45) Date of Patent: Jan. 7, 2025

(54) HYDROGENATION CATALYST USED IN AMIDE COMPOUND HYDROGENATION AND METHOD FOR PRODUCING AMINE COMPOUND USING SAME

(71) Applicants: OSAKA UNIVERSITY, Osaka (JP); N.E. CHEMCAT CORPORATION, Tokyo (JP)

(72) Inventors: Kiyotomi Kaneda, Osaka (JP); Takato Mitsudome, Osaka (JP); Miho Kimura, Osaka (JP); Yukio Takagi, Tokyo (JP); Yosuke Imanaka, Tokyo (JP); Hiroyasu Suzuka, Tokyo (JP); Tatsuya Kojima, Tokyo (JP)

(73) Assignees: Osaka University, Osaka (JP); N.E. Chemcat Corporation, Tokyo (JP)

( * ) Notice: Subject to any disclaimer, the term of this patent is extended or adjusted under 35 U.S.C. 154(b) by 758 days.

(21) Appl. No.: 17/433,126

(22) PCT Filed: Feb. 20, 2020

(86) PCT No.: PCT/JP2020/006760
§ 371 (c)(1),
(2) Date: Aug. 23, 2021

(87) PCT Pub. No.: WO2020/175309
PCT Pub. Date: Sep. 3, 2020

(65) Prior Publication Data
US 2022/0144789 A1    May 12, 2022

(30) Foreign Application Priority Data

Feb. 26, 2019 (JP) ................ 2019-032959
Jun. 3, 2019 (JP) ................ 2019-103938
Jul. 31, 2019 (JP) ................ 2019-140449

(51) Int. Cl.
| | | |
|---|---|---|
| *C07D 295/023* | (2006.01) | |
| *B01J 27/18* | (2006.01) | |
| *B01J 27/19* | (2006.01) | |
| *B01J 37/02* | (2006.01) | |
| *B01J 37/04* | (2006.01) | |
| *C07D 487/04* | (2006.01) | |

(52) U.S. Cl.
CPC ...... *C07D 295/023* (2013.01); *B01J 27/1806* (2013.01); *B01J 27/19* (2013.01); *B01J 37/0244* (2013.01); *B01J 37/04* (2013.01); *C07D 487/04* (2013.01)

(58) Field of Classification Search
CPC .................................... C07D 295/023
USPC ............................................. 544/178
See application file for complete search history.

(56) References Cited

FOREIGN PATENT DOCUMENTS

| | | |
|---|---|---|
| JP | H08-245524 A | 9/1996 |
| JP | H09-241222 A | 9/1997 |
| JP | 2012-121843 A | 6/2012 |
| JP | 2012-140419 A | 7/2012 |
| JP | 2016-160243 A | 9/2016 |
| WO | 2005/066112 A1 | 7/2005 |

OTHER PUBLICATIONS

Extended European Search Report issued by the European Patent Office on Oct. 28, 2022, in connection with European Patent Application No. 20762503.9.
T. Mizugaki et al., Selective Hydrogenation of Levulinic Acid to 1,4-Pentanediol in Water Using a Hydroxyapatite-Supported Pt—Mo Bimetallic Catalyst, Green Chemistry, Jan. 2015, pp. 5136-5139, vol. 17, No. 12, United Kingdom.
International Search Report Issued in PCT/JP2020/006760 on Apr. 28, 2020.
Written Opinion Issued in PCT/JP2020/006760 on Apr. 28, 2020.
R. Burch et al.; Catalytic Hydrogenation of Tertiary Amides at Low Temperatures and Pressures Using Bimetallic Pt/Re-Based Catalysts; Journal of Catalysis; 2011; pp. 89-97; 283; UK.
Mario Stein et al.; Catalytic Hydrogenation of Amides to Amines under Mild Conditions; Angew. Chem. Int. ed.; 2013; pp. 2231-2234; 52; Germany.
Ekambaram Balaraman et al.; Direct Hydrogenation of Amides to Alcohols and Amines under Mild Conditions; J. Am. Chem. Soc.; 2010; pp. 16756-16758; vol. 132, No. 47; USA.
Yoshinao Nakagawao et al.; Combination of Supported Bimetallic Rhodium-Molybdenum Catalyst and Cerium Oxide for Hydrogenation of Amide; 2015; Sci. Technol. Adv. Mater.; pp. 1-7; Focus Issue Paper 16, 014901; Japan.
Chitaru Hirosawa et al.; Hydrogenation of Amides by the Use of Bimetallic Catalysts Consisting of Group 8 to 10, and Group 6 or 7 Metals; Tetrahedron Letters; 1996; pp. 6749-6752; vol. 37, No. 37; Great Britain.

*Primary Examiner* — Taofiq A Solola
(74) *Attorney, Agent, or Firm* — Edwards Neils LLC; Jean C. Edwards, Esq.

(57) ABSTRACT

Provided is a catalyst for amide compound hydrogenation characterized in that rhodium and molybdenum are supported on hydroxyapatite, the catalyst for amide compound hydrogenation providing a catalyst that can promote a reduction reaction that converts an amide compound into an amine compound, can be used under moderate conditions, and has durability that allows repeated use thereof while retaining high activity. Also provided is a method for producing an amine compound, the method being characterized by including bringing an amide compound into contact with the catalyst for amide compound hydrogenation to cause hydrogenation, thereby producing an amine compound.

2 Claims, 2 Drawing Sheets

HYDROGENATION CATALYST USED IN AMIDE COMPOUND HYDROGENATION AND METHOD FOR PRODUCING AMINE COMPOUND USING SAME

TECHNICAL FIELD

The present invention relates to a catalyst for use in a hydrogenation reaction that converts an amide compound into an amine compound, the catalyst containing rhodium and molybdenum and being supported on hydroxyapatite, and also relates to a method for producing an amine compound using the catalyst.

BACKGROUND ART

A reduction reaction that converts an amide compound into an amine compound is one of the most difficult reactions in reduction of carboxylic acid derivatives since amides are resistant to reduction.

In a small scale experiment, like in research, such a reduction reaction that converts an amide compound into an amine compound is generally achieved by a method using a strong reductant, such as lithium aluminum hydride (LiAlH$_4$) or sodium borohydride (NaBH$_4$), on a stoichiometric basis. However, when such a method is used in an industrial scale synthesis, there are problems, for example, in that the method causes generation of a large amount of metallic waste and such a reductant, if used in a large amount, is dangerous because of its high reactivity, which leads to generation of hydrogen and the like, and in that a complex post-treatment operation and the like is required.

On the other hand, the reduction reaction from an amide to an amine in which molecular hydrogen is used as a reductant produces only nontoxic water as a byproduct, and thus is an environmentally friendly method for synthesizing an amine. This catalytic hydrogen reduction reaction of amides has been studied for a long period, and has been conducted using cupper-chromium, rhenium, or nickel catalysts. Such a reaction however requires reaction conditions of a high pressure and a high temperature, for example, a hydrogen pressure of 200 atm and a reaction temperature of 200° C. or higher.

In recent years, NPLs 1 and 2 have reported that, when molecular sieve is added to a reaction system, hydrogenation of an amide can be achieved under a low temperature and low pressure condition, for example, 120° C. and 10 atm, or 160° C. and 5 atm. Such a method however has had a problem of poor substrate compatibility and producing an alcohol as a byproduct by the C—N cleavage. In addition, such a catalyst cannot be reused.

There is a reaction using a homogeneous catalyst as reported in NPL 3, but there has been a problem of producing an alcohol as a byproduct by the C—N cleavage. In addition, in a reaction using a homogeneous catalyst, it is difficult to repeatedly use the catalyst which is expensive.

Regarding such amide hydrogenation, besides the above catalyst, there are reports on a reaction using a heterogeneous catalyst with a carrier that is generally widely used, such as silica (NPL 4) and a reaction using a homogeneous catalyst with various carbonate salts (NPL 5). However, some are inferior in conversion and yield, some require a high temperature condition in use, and thus, none of them satisfies the market demand.

Thus, a catalyst that can be used even under moderate conditions and that has durability that allows repeated use thereof while retaining high activity is required for industrial use.

CITATION LIST

Non-Patent Literature

NPL 1: R. Burch, C. Paun, X.-M. Cao, P. Crawford, P. Goodrich, C. Hardacre, P. Hu, L. McLaughlin, J. Sa, J. M. Thompson, Catalytic hydrogenation of tertiary amides at low temperatures and pressures using bimetallic Pt/Re-based catalysts. J. Catal. 283, 89-97 (2011)

NPL 2: M. Stein, B. Breit, Catalytic hydrogenation of amides to amines under mild conditions. Angew. Chem. Int. Ed. 125, 2287-2290 (2013)

NPL 3: E. Balaraman, B. Gnanaprakasam, L. J. W. Shimon, D. Milstein, Direct hydrogenation of amides to alcohols and amines under mild conditions. J. Am. Chem. Soc. 132, 16756-16758 (2010)

NPL 4: Y. Nakagawao, M. Tamura, K. Tomishige et al. Sci. Technol. Adv. Mater. 2015, 16, 014901

NPL 5: C. Hirosawa, N. Wakana, T. Fuchikami, Tet. Lett. 1996, 37, 6749-6752

SUMMARY OF INVENTION

Technical Problem

Accordingly, the present invention has an object to provide a catalyst that can promote a reduction reaction that converts an amide compound into an amine compound, that can be used even under moderate conditions, and that has durability that allows repeated use thereof while retaining high activity.

Solution to Problem

As a result of intensive and extensive studies for solving the above problem, the present inventors have found that a catalyst containing hydroxyapatite, and rhodium and molybdenum that are supported on the hydroxyapatite has high hydrogenation activity, selectivity, durability, and reactivity on an amide compound, completing the present invention.

Specifically, the present invention relates to a catalyst for amide compound hydrogenation, the catalyst containing hydroxyapatite, and rhodium and molybdenum that are supported on the hydroxyapatite.

In addition, the present invention relates to a method for producing the catalyst for amide compound hydrogenation, the method including allowing rhodium and molybdenum to be supported on hydroxyapatite in a solvent, and then drying the resultant.

Furthermore, the present invention also relates to a method for producing an amine compound, the method including bringing an amide compound into contact with the catalyst for amide compound hydrogenation to cause hydrogenation of the amide compound, thus producing an amine compound.

Advantageous Effects of Invention

Since the catalyst of the present invention can be used under moderate conditions, synthesis of an amine compound from an amide compound can be achieved in a safe and easy manner.

In addition, since the catalyst of the present invention requires no special operation in production thereof, the catalyst can be produced in an inexpensive and safe manner.

Thus, the catalyst of the present invention can be used in an industrial synthesis of an amine compound from an amide compound.

In addition, in the catalyst of the present invention, expensive rhodium can be easily collected by filtration after use since the catalyst is supported on hydroxyapatite, and the collected catalyst can retain the initial activity and selectivity.

Accordingly, the catalyst of the present invention can be readily reused.

DESCRIPTION OF EMBODIMENTS

Figure 1:
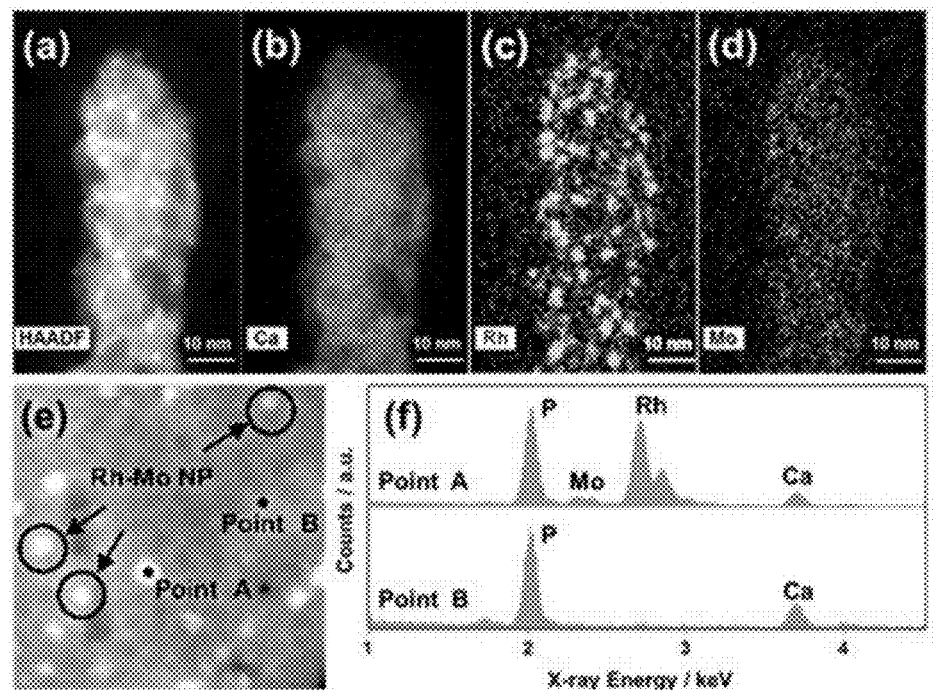
FIG. 1 It shows ADF-STEM images and an EDX analytic result of a catalyst of the present invention having undergone a hydrogen reduction treatment.

A catalyst for amide compound hydrogenation of the present invention (hereinafter referred to as "the catalyst of the present invention") contains hydroxyapatite, and rhodium and molybdenum that are supported on the hydroxyapatite. The catalyst of the present invention is herein sometimes denoted as, for example, "X—Y/HAP" (X and Y are each a name of metal, such as rhodium or molybdenum, and HAP is hydroxyapatite).

(Rhodium)

Rhodium that constitutes the catalyst of the present invention is not particularly limited, but is preferably, for example, rhodium particles. As used herein, rhodium particles are particles of rhodium selected from at least one of metallic rhodium or rhodium oxide, and are preferably particles of metallic rhodium.

Here, the rhodium particles are not particularly limited as long as the particles contain rhodium, and may contain a small amount of a noble metal, such as ruthenium (Ru), platinum (Pt), or palladium (Pd). The rhodium particles are preferably metallic rhodium particles. The rhodium particles may be primary particles or may be secondary particles. The rhodium particles preferably have an average particle size of 1 to 30 nm, and more preferably 1 to 10 nm. Note that the "average particle size", as used herein, means an average of diameters obtained by observing any number of particles with an electron microscope.

(Molybdenum)

Molybdenum that constitutes the catalyst of the present invention is not particularly limited, but may include molybdenum in the form of oxide, such as $MO_3$, but is preferably particles of metallic molybdenum.

(Rhodium-Molybdenum)

In a reduction state where the catalyst of the present invention is used, Rh and Mo are both preferably contained in the metallic state. NPL 5 as described above reports that Rh and Mo both exhibit excellent hydrogenation performance in the metallic state, in other words, in the zero-valent state.

(Molar Ratio of Rhodium-Molybdenum [Rh—Mo])

The compositional ratio of rhodium and molybdenum in the catalyst of the present invention in terms of number of moles of rhodium (Rh) as metal: number of moles of molybdenum (Mo) as metal (molar ratio [Rh:Mo]) is preferably 1:0.01 to 1, more preferably 1:0.05 to 0.5, and further preferably 1:0.05 to 0.2

(Hydroxyapatite)

A carrier (base material) of the catalyst of the present invention is hydroxyapatite (HAP). The hydroxyapatite may have an adsorption ability, as measured as the so-called BET value, of 0.1 to 300 $m^2/g$, and may have an average particle size of 0.02 to 100 µm. In the present invention, the adsorption ability of the hydroxyapatite is preferably 0.5 to 180 $m^2/g$, and further preferably 30 to 100 $m^2/g$. Note that, in place of hydroxyapatite, another apatite, such as chloroapatite or fluoroapatite, can, of course, be used as a carrier in the catalyst of the present invention.

In addition, the form of the hydroxyapatite is not particularly limited, and examples of the form include a powder form, a spherical particle form, an amorphous granular form, a cylindrical pellet form, an extruded shape, and a ring shape.

The hydroxyapatite is not particularly limited, and includes, not only calcium hydroxyphosphate having a general stoichiometric composition, $Ca_{10}(PO_4)_6(OH)_2$, but also a calcium hydroxyphosphate compound having a composition similar to the above composition, tricalcium phosphate, and the like.

In the catalyst of the present invention, the aspect of rhodium and molybdenum supported on the hydroxyapatite is not particularly limited, and various aspects can be employed according to the form of the hydroxyapatite. The position of supporting also does not have to be simply controlled, and may be on the inside of pores or a layer or may be only on the surface. However, it is preferred that rhodium having a small particle size be supported in a dispersed manner and molybdenum be present in the vicinity of the rhodium or on the rhodium.

Note that the amounts of rhodium and molybdenum supported on the carrier in the catalyst of the present invention are not particularly limited, but as the amount of molybdenum supported in terms of metal is larger, the yield increases. Thus, the amount of molybdenum supported in the catalyst of the present invention is preferably 0.01 mmol/g or more based on the carrier, and more preferably 0.015 mmol/g or more. Note that the upper limit of the amount of molybdenum supported in the catalyst of the present invention is not particularly limited, but, for example, is preferably 0.04 mmol/g or less, and more preferably 0.03 mmol/g.

Since the catalyst of the present invention uses such a hydroxyapatite as described above, separation is easily achieved after the catalyst is used in a reaction, and the catalyst is obviously advantageous in terms of reuse of the catalyst.

(Component that can be Added to the Catalyst)

The catalyst of the present invention may be any catalyst as long as rhodium and molybdenum as described above are supported on hydroxyapatite. A transition metal, an alkali metal, an alkaline earth metal, or the like may be incorporated as a component of the catalyst or a component of the hydroxyapatite according to an ordinary method to the extent that the effect is not impaired.

(Method for Producing the Catalyst of the Present Invention)

Among the catalysts of the present invention, a catalyst for amide compound hydrogenation characterized in that rhodium and molybdenum are supported on hydroxyapatite can be produced by allowing rhodium and molybdenum to be supported on hydroxyapatite in a solvent, and then drying the resultant (hereinafter referred to as "the inventive method"). Note that a firing treatment may be applied after drying.

In the inventive method, a specific method for allowing rhodium and molybdenum to be supported on hydroxyapatite in a solvent is not particularly limited, and examples thereof include a method of adding to and mixing with hydroxyapatite a solvent mixture liquid containing a rhodium compound and a molybdenum compound solution to allow rhodium and molybdenum to be supported on the hydroxyapatite in a solvent, and a method of separately mixing hydroxyapatite, a solvent liquid containing a rhodium compound, and a solvent liquid containing a molybdenum compound in any order to allow rhodium and molybdenum to be supported on the hydroxyapatite in a solvent.

The rhodium compound used in the inventive method is not particularly limited, but is preferably a compound that forms rhodium particles on hydroxyapatite upon drying. Examples of the rhodium compound include salts, such as potassium hexachlororhodate(III) ($K_3[RhCl_6]\cdot xH_2O$), rhodium trichloride·hydrate ($RhCl_3\cdot xH_2O$), hexachlororhodic (III) acid ($H_3[RhCl_6]$), sodium hexachlororhodate(III) ($Na_3[RhCl_6]\cdot xH_2O$), ammonium hexachlororhodate(III) ($(NH_4)_3[RhCl_6]\cdot xH_2O$), pentachloroaquarhodic(III) acid ($H_2[RhCl_5(H_2O)]$), sodium pentachloroaquarhodate(III) ($Na_2[RhCl_5(H_2O)]$), potassium pentachloroaquarhodate(III) ($K_2[RhCl_5(H_2O)]$), ammonium pentachloroaquarhodate(III) (($NH_4)_2[RhCl_5(H_2O)]$), rhodium(III) nitrate($Rh(NO_3)_3$), rhodium (III) sulfate ($Rh_2(SO_4)_3$), rhodium(III) acetate ($Rh(CH_3COO)_3$), rhodium(II) acetate ($Rh_2(CH_3COO)_4$), tris(2, 4-pentanedionato)rhodium (III) ($Rh(acac)_3$), dexarhodium hexadecacarbonyl ($Rh_6(CO)_{16}$), and (acetylacetonato)dicarbonyl rhodium ($[Rh(C_5H_7O_2)(CO)_2]$).

The molybdenum compound used in the inventive method is not particularly limited, but is preferably a compound that produces molybdenum oxide on hydroxyapatite upon drying. Examples of the molybdenum compound include salts, such as hexaammonium heptamolybdate (($NH_4)_6Mo_7O_{24}\cdot xH_2O$), sodium molybdate ($Na_2MoO_4$), potassium molybdate ($K_2MoO_4$), ammonium molybdate (($NH_4)_2MoO_4$), sodium heptamolybdate ($Na_6Mo_7O_{24}\cdot xH_2O$), potassium heptamolybdate ($K_6Mo_7O_{24}\cdot xH_2O$), ammonium heptamolybdate (($NH_4)_6Mo_7O_{24}\cdot xH_2O$), sodium octamolybdate ($Na_4Mo_8O_{16}\cdot xH_2O$), potassium octamolybdate ($K_4Mo_8O_{16}\cdot xH_2O$), ammonium octamolybdate (($NH_4)_4Mo_8O_{16}\cdot xH_2O$), potassium tetramolybdate ($K_2Mo_4O_{13}$), molybdenum(IV) oxalate ($MoO(C_2O_4)\cdot xH_2O$), molybdenum(II) acetate ($Mo(CH_3COO)_2$), and molybdenum hexacarbonyl ($Mo(CO)_6$).

A solution containing a rhodium compound and a molybdenum compound used in the inventive method is a suspension of the rhodium compound and the molybdenum compound in a solvent. The molar ratio of the rhodium compound and the molybdenum compound in the solution is preferably 1:0.5 to 10, more preferably 1:1 to 8, and further preferably 1:4 to 7 in terms of the molar ratio of rhodium to molybdenum as metals [Rh:Mo]. Examples of the solvent include water and an organic solvent, such as an alcohol or acetone. Water, which is superior both in the cost and safety, is preferred. Such a solvent may be used alone or two or more of such solvents may be used in combination. The temperature of the solvent is not particularly limited, but, for example, the temperature is 0 to 100° C., and preferably 10 to 80° C.

The solution prepared as described above may then be mixed with hydroxyapatite. The method for mixing the solution and hydroxyapatite is not particularly limited as long as all the components are sufficiently dispersed. For rhodium, hydroxyapatite in an amount of 0.1 to 100 g, and preferably 1 to 10 g relative to 0.1 mmol of rhodium as metal may be used. For molybdenum, hydroxyapatite in an amount of 0.1 to 100 g, preferably 1 to 10 g relative to 0.5 mmol of molybdenum as metal may be used. Mixing of hydroxyapatite, a rhodium compound, and a molybdenum compound may be achieved by stirring, and impregnation may be promoted by applying ultrasonic waves. The stirring time in mixing by stirring is not particularly limited, but may be 0.5 to 24 hours, preferably 1 to 20 hours. In addition, the application time in impregnation with ultrasonic waves is not particularly limited, but may be several minutes to several hours. Note that both of such a physical mixing and the ultrasonic application may be used in combination in any order. Such a rhodium compound and a molybdenum compound may each be separately mixed with hydroxyapatite, or may be mixed as a mixture solution with hydroxyapatite.

A solvent liquid containing a rhodium compound and a solvent liquid containing a molybdenum compound used in the inventive method are a liquid in which the rhodium compound and the molybdenum compound are each suspended in a solvent. The contents of the respective compounds in the solvent liquids may be the same either when the solvent liquids are mixed or when impregnation with the rhodium compound and impregnation with the molybdenum compound are separately performed. In addition, the solvent used therein and the temperature of the solvent may be the same as in the above solvent mixture liquid.

When a solvent liquid containing a rhodium compound and a solvent liquid containing a molybdenum compound prepared as described above are separately mixed, hydroxyapatite, the solvent liquid containing a rhodium compound, and the solvent liquid containing a molybdenum compound may be mixed in any order. An order in which the hydroxyapatite and the solvent liquid containing a rhodium compound are mixed first and then the mixture is mixed with the solvent liquid containing a molybdenum compound is advantageous in that molybdenum tends to be supported on the rhodium compound. An order in which the rhodium compound is mixed earlier than the molybdenum compound is advantageous in that the loss of the expensive rhodium may be reduced. The method for mixing the solvent liquid and hydroxyapatite may be the same as in the case of using the mixture solution.

After the solvent mixture liquid is mixed with hydroxyapatite or each solvent liquid is mixed with hydroxyapatite to allow rhodium and molybdenum to be supported on hydroxyapatite in a solvent as described above, the resultant may be dried. Before drying, a pretreatment, such as washing, filtration, or concentration, is preferably performed to remove the solvent. The condition of drying is not particularly limited, but, for example, drying is performed at 80 to 200° C. for 1 to 56 hours. After drying, the catalyst may be subjected to firing, and in an example of firing, the catalyst may be fired using a muffle furnace or the like at 250 to 700°

C. for 1 to 12 hours, and following drying or firing, the resultant may further be subjected to pulverization, classification, or the like.

A preferred example of the rhodium compound in the case where water is used as a solvent in the inventive method is potassium hexachlororhodate(III) trihydrate ($K_3[RhCl_6] \cdot 3H_2Oaq$). A preferred example of the molybdenum compound is hexaammonium heptamolybdate tetrahydrate (($NH_4)_6Mo_7O_{24} \cdot 4H_2Oaq$).

In addition, when water is used as a solvent in the inventive method, if the compound is difficult to dissolve in the solvent, a pH adjuster, a binder, or the like may be used, ultrasonic waves may be applied, or the temperature may be adjusted, to the extent that the catalytic performance is not impaired. Examples of the pH adjuster include sodium hydroxide, sodium carbonate, sodium hydrogen carbonate, potassium carbonate, potassium hydrogen carbonate, ammonia, acetic acid, citric acid, carbonic acid, and lactic acid. Examples of the binder include an organic compound, such as polyethylene glycol or polyvinyl alcohol, and an inorganic compound, such as silica.

The catalyst of the present invention may be any catalyst as long as rhodium and molybdenum (hereinafter simply referred to as "rhodium, etc.") are supported on hydroxyapatite, and thus the supported rhodium, etc. may be of zero valent, may be alloyed, may not be alloyed, or may be partially alloyed. The catalyst preferably contains zero-valent rhodium, etc. and alloyed rhodium, etc. Rhodium, etc. may be uniformly supported in hydroxyapatite or may be biasedly supported on the surface side of hydroxyapatite. Regarding the position of supporting rhodium, etc., it is desirable that the component be biasedly supported on the surface side of hydroxyapatite, particularly when expensive components, such as rhodium, etc., are to be effectively used. Biased support on the hydroxyapatite surface increases the chance of a reaction substrate to come in contact with rhodium, etc., whereby an increase in the catalytic activity is expected.

When rhodium, etc. is biasedly supported on the hydroxyapatite surface, the method is not particularly limited, and can be appropriately selected from known techniques according to the catalyst material used. Specific examples thereof include a technique in which the pH of the solvent mixture liquid containing a rhodium compound and a molybdenum compound or the pH of the solvent liquid containing a rhodium compound and the pH of the solvent liquid containing a molybdenum compound is(are) adjusted, a method in which, for insolubilizing (precipitating) rhodium, etc. on hydroxyapatite, a treatment with an aqueous solution to be used for insolubilization, such as an aqueous alkali solution, is performed to immobilize the rhodium, etc. before or after mixing the solvent mixture liquid or the solvent liquids with hydroxyapatite, a technique in which the temperature and the settling time are controlled to perform aging after mixing the solvent mixture liquid or the solvent liquids with the hydroxyapatite, and a technique in which a firing step is further added after producing the catalyst of the present invention. Note that in the above techniques, washing, drying, and the like may be appropriately performed.

When the pH(s) of the solvent mixture liquid or the solvent liquids is(are) adjusted, in the technique therefor, the pH adjuster as described above can be used. The pH(s) of the solvent mixture liquid or the solvent liquids may be adjusted using the pH adjuster so that support on hydroxyapatite is easily achieved. The pH may be made acidic, alkaline, or neutral.

When a treatment with an aqueous solution to be used for insolubilization, such as an aqueous alkali solution, is performed before or after mixing the solvent mixture liquid or the solvent liquids with hydroxyapatite, in the technique therefor, an aqueous alkali solution in which an alkaline compound is dissolved in water or the like is used. Examples of the alkaline compound include a hydroxide of an alkali metal or an alkaline earth metal, a bicarbonate of an alkali metal or an alkaline earth metal, a carbonate of an alkali metal or an alkaline earth metal, a silicate of an alkali metal or an alkaline earth metal, and ammonia. The pH in this case is not particularly limited, but is 7 to 14, and preferably 8 to 13.

When the treatment for insolubilization is performed, regarding the amount of the aqueous alkali solution used therein, since the purpose is to immobilize a rhodium compound and a molybdenum compound, an aqueous alkali solution having a concentration adjusted so that the amount of alkali is slightly excess, for example, 1.05 to 1.2 times, relative to the substance to be reduced is preferably used.

When aging is performed, in the technique therefor, the temperature and the settling time after mixing the solvent mixture liquid or the solvent liquids with the hydroxyapatite may be appropriately set and are not particularly limited, but, for example, ageing may be performed at 10 to 100° C. for 1 to 72 hours, and preferably at 30 to 70° C. for 2 to 24 hours.

When a firing step is further added after producing the catalyst of the present invention, in a technique therefor, the produced catalyst of the present invention may be fired while applying a heat reduction treatment in a gas atmosphere containing hydrogen. Such firing is also referred to as gas phase reduction or hydrogen reduction. In the case of gas phase reduction, there is no solvent that mediates the reduction and the component to be reduced is difficult to move so that particles of the rhodium, etc. hardly aggregate. This can allow the rhodium, etc. to be supported in the form of small particles.

When the firing step is performed, the rhodium, etc. are sometimes oxidized through firing. In this case, a reduction treatment is preferably applied. In the reduction treatment, gas phase reduction and liquid phase reduction can be employed. In gas phase reduction, a reductive gas is supplied to the catalyst heated to 100 to 500° C. to apply a reduction treatment. As the reductive gas, in addition to hydrogen as described above, carbon monoxide or a low molecular weight hydrocarbon may be used. As the low molecular weight hydrocarbon, methane, ethane, propane, butane, ethylene, or the like can be used. In the case of gas phase reduction, the composition of the gas phase used may be constituted only of a reductive component, or a composition in which a reductive component is mixed with a gas that is inactive in reduction, such as nitrogen, may be used, or the reduction may be performed by supplying hydrogen to the catalyst mixed with a solvent in a heated and pressurized state.

In liquid phase reduction, a reductive liquid and the catalyst are mixed and heated to 80 to 150° C. to reduce an oxidized catalyst component. The reductive component used is not particularly limited, and may be appropriately selected depending on the reduction conditions. Examples thereof include formic acid, sodium formate, and hydrazine.

A heat reduction treatment may be performed by heating in an organic solvent having hydrogen added therein under a pressurized state.

By performing such a heat reduction treatment during, after, or in place of a firing step, rhodium and molybdenum which are not alloyed are reduced into the zero-valent (metal) state.

The thus obtained catalyst of the present invention contains hydroxyapatite, and rhodium and molybdenum supported thereon.

Note that the production of the catalyst of the present invention can be confirmed, for example, by a transmission electron microscope (TEM), a field emission-scanning electron microscope (FE-SEM), energy dispersive x-ray spectroscopy (EDX), or the like. Furthermore, the state of the catalyst of the present invention during a hydrogenation reaction can be analyzed by X-ray absorption fine structure (XAFS).

The present inventors subjected a catalyst (Rh—Mo/HAP) obtained in Production Example 1 as described later to a structural analysis based on X-ray absorption fine structure (XAFS) in a reduction state that simulates the state used in hydrogenation which is its preferred aspect.

When the X-ray absorption near edge structure (XANES) was analyzed in a region of about ±50 eV of the absorption edge in XAFS of Rh—Mo/HAP of the present invention, the energy of Mo at the absorption edge was close to that of metal Mo (metal Mo foil). It was thus found that Mo in Rh—Mo/HAP of the present invention contains zero-valent Mo during hydrogenation reaction.

Similarly, Rh in Rh—Mo/HAP of the present invention was also analyzed by XANES. Then, the energy at the absorption edge coincided with that of metal Rh (Rh foil), and it was found that Rh also contains zero-valent Rh during hydrogenation reaction.

Furthermore, for Mo in Rh—Mo/HAP of the present invention, the extended X-ray absorption fine structure (EXAFS) in a region from the absorption edge of XAFS to about 1000 eV was analyzed. Then, a peak attributable to the Mo—Mo bond was seen. It was thus found that Mo atoms form a cluster at least during hydrogenation reaction.

Similarly, EXAFS was analyzed also for Rh in Rh—Mo/HAP of the present invention. Then, a peak attributable to the Rh—Rh bond was seen. It was thus found that Rh atoms also form a cluster at least during hydrogenation reaction.

As a result of such a particular structural analysis by XAFS, it was found that Rh—Mo/HAP of the present invention contains Rh and Mo as zero-valent clusters during hydrogenation reaction.

Although the reason why the catalyst can exhibit such an excellent performance is not clear, the analytic results have suggested the existence of alloyed rhodium and molybdenum. In addition, besides the existence of such an alloy, the existence of the zero-valent rhodium and molybdenum which are produced through reduction of Rh—Mo/HAP before the reaction or in the reaction system is also considered as one of promoting factors of selective hydrogenation of an amide compound by the catalyst of the present invention.

(Hydrogenation of Amide Compound)

The catalyst of the present invention is for a hydrogenation reaction of an amide compound. Thus, when the catalyst of the present invention is brought into contact with an amide compound, the amide compound can be hydrogenated (reduced) to produce an amine compound.

The amide compound is not particularly limited as long as it is a compound having an amide bond, but, for example, a secondary or higher amide compound, an amide compound having an aromatic substituent, an amide compound in which two substituents excluding the carbonyl bonded to the N atom in a lactam or tertiary amide are bonded to each other to form a cyclic structure, or the like is preferred. A secondary or higher amide compound or an amide compound having an aromatic substituent is more preferred. Note that among amide compounds, an amide compound that contains no unsaturated hydrocarbon group is expected to be increased in the yield since the hydrogenation easily has an effect only on the oxygen in the oxo acid structure.

The method for bring the catalyst of the present invention into contact with an amide compound to hydrogenate the amide compound is not particularly limited and may be appropriately selected. Specifically, in a pressure resistant vessel, such as an autoclave, the catalyst of the present invention and an amide compound are brought into contact with hydrogen gas in a liquid phase to thereby cause hydrogenation of the amide compound. In addition, in the hydrogenation, the amide compound may be brought into contact also with molecular sieve which is previously placed in the vessel, for removing water to promote the reaction. Furthermore, the catalyst of the present invention may be previously subjected to a reduction treatment before hydrogenation. Molecular sieve is used for absorbing water produced in the reaction. The amount of molecular sieve is not particularly limited, but in order to securely absorb water produced in the reaction, with molecular sieve fully dried, the amount is preferably appropriately determined according to the amount of water produced in the reaction. The type of the molecular sieve used is preferably selected so that the substrate and product are not absorbed thereto.

The amount of the molecular sieve used is not particularly limited as long as the reaction proceeds, but a large excess amount relative to the theoretical amount of water produced is preferably used. For example, the amount may be preferably 1 to 200 times as large as the minimum amount of the molecular sieve required which is calculated based on the maximum absorption, more preferably 3 to 150 times, and further preferably 5 to 100 times.

The liquid phase preferably includes only an organic solvent or a blend liquid of plural organic solvents, and more preferably only an organic solvent. The organic solvent used above is not particularly limited, but examples thereof include one or more selected from an aliphatic hydrocarbon having 5 to 20 carbon atoms, such as dodecane or cyclohexane; an aromatic hydrocarbon having 7 to 9 carbon atoms, such as toluene or xylene; an ether having a chain structure or a cyclic structure, such as dimethyl ether, dimethoxyethane (DME), diethoxyethane, dibutoxyethane, diglyme, cyclopentyl methyl ether, oxetane, tetrahydrofuran (THF), tetrahydropyran (THP), furan, dibenzofuran, or furan; and a polyether, such as polyethylene glycol or polypropylene glycol. Among then, DME is particularly preferred.

The amount of the organic solvent used is preferably, for example, in the range that gives a concentration of the amide compound of about 0.5 to 2.0% by mass. The amount of the catalyst of the present invention used based on the amount of rhodium in the catalyst is preferably, for example, about 0.0001 to 50% by mole relative to the amide compound, preferably about 0.01 to 20% by mole, and more preferably about 0.1 to 5% by mole.

The catalyst of the present invention can smoothly promote hydrogenation reaction even under moderate conditions. The reaction temperature can be appropriately adjusted according to the type of the substrate or the type of the target product. For example, the reaction temperature is 200° C. or lower, preferably 10 to 180° C., more preferably about 20 to 160° C., and particularly preferably about 30 to 150° C. The pressure during reaction is 5 MPa or less, preferably 0.1 which is a normal pressure to 4 MPa, and more preferably 0.1 to 3.5 MPa. The reaction time can be appropriately adjusted according to the reaction temperature and pressure, and is, for example, about 10 minutes to 56 hours, preferably about 20 minutes to 48 hours, and particularly preferably about 40 minutes to 30 hours.

By the above method, an amide compound can be hydrogenated to obtain an amine compound, and even an amine compound that is difficult to produce by a general cross coupling reaction and the like can be produced by the method of the present invention. Specifically, in the Buchwald-Hartwig reaction which is a typical example of C—N coupling, a halogenated aryl and a primary or secondary amine can be reacted in the presence of a Pd catalyst to allow the aryl group to directly bond to the N atom of the amine, but it is not possible to incorporate one or more carbon atoms or a methylene chain between the N atom and the aromatic ring. However, in the above method, when the amide compound obtained by acylating the N atom of an amine is hydrogenated, as a result, a C—N bond with one or more carbon atoms or a methylene chain incorporated adjacent to the N atom of the original amine can be produced. Examples of such reactions include the following: morpholine→4-cyclohexylcarbonylmorpholine→4-cyclohexylmethylmorpholine, piperidine→1-phenylacetylpiperidine→1-phenetylpiperidine, and benzylmethylamine→benzylmethylphenylacetylamide→benzylmethylphenetylamine.

(Reuse of Catalyst)

In the catalyst of the present invention, since rhodium which is an active component is supported on hydroxyapatite, the rhodium supported hardly forms larger particles even in the reaction. In addition, the catalyst of the present invention can be easily collected by, for example, a physical separation technique, such as filtration or centrifugation, from the reaction liquid after hydrogenation. The collected catalyst of the present invention can be reused as it is or after subjected to washing, drying, firing, or the like, as required. Washing, drying, firing, or the like may be achieved in the same manner as in the production of the catalyst of the present invention.

The collected catalyst of the present invention can exhibit almost the same catalytic ability as compared with the fresh catalyst of the present invention, and even after use-regeneration is repeated plural times, decrease in the catalytic ability can be significantly suppressed. Thus, according to the present invention, a catalyst which generally occupies a large proportion of the cost of hydrogenation can be collected and repeatedly used, thereby making it possible to greatly reduce the cost of hydrogenation of an amide compound.

EXAMPLES

The catalyst of the present invention and the examples of the present invention will be specifically described below, but the present invention is not to be limited to the following examples and can be applied in the scope of the gist of the present invention.

Production Example 1

Preparation of Rh—Mo/HAP:

Into a 100-ml eggplant flask containing 80 ml of distilled water, 0.2 mmol of $(K_3[RhCl_6])·3H_2Oaq$ manufactured by N.E. CHEMCAT CORPORATION was added and was subjected to an ultrasonic treatment for 3 minutes. Then, 1.0 g of HAP from Wako Pure Chemical Corporation (trade name "Tricalcium Phosphate") was added with vigorous stirring and the mixture was heated to 80° C. After stirring in this state for 15 hours, the mixture was allowed to stand for 1.5 hours to be cooled to room temperature. To the cooled solution, 25 ml of $(NH_4)_6Mo_7O_{24}·4H_2Oaq$ (40 mM) (Mo content: 1.0 mmol) was added dropwise, and then the mixture was heated to 50° C. and was stirred for 3 hours. After stirring, the mixture was filtered, and was washed by filtration with about 1 L of distilled water. The residue after the filtration washing was dried at 120° C. for 8 hours or more to obtain Rh—Mo/HAP (Rh: 0.2 mmol/g, Mo: 0.017 mmol/g).

Production Examples 2 to 6

Preparation of Comparative Bimetal/HAP Catalyst:

A Rh—Re/HAP catalyst, a Rh—V/HAP catalyst, a Pt—Mo/HAP catalyst, a Pd—Mo/HAP catalyst, and a Ru—Mo/HAP catalyst were obtained in the same manner as in Production Example 1 except for using $NH_4ReO_4$ as a rhenium salt, $NH_4VO_3$ as a vanadium salt, $K_2PtCl_4$ as a platinum salt, $K_2PdCl_6$ as a palladium salt, or $K_2RuCl_6$ as a ruthenium salt.

Production Example 7

Preparation of Comparative Rh/HAP:

Into a 100-ml eggplant flask containing 80 ml of distilled water, 0.2 mmol of $K_3[RhCl_6]$ manufactured by N.E. CHEMCAT CORPORATION was added and was subjected to an ultrasonic treatment for 3 minutes. Then, 1.0 g of HAP from Wako Pure Chemical Corporation (trade name "Tricalcium Phosphate") was added with vigorous stirring and the mixture was heated to 70° C. After stirring in this state for 15 hours, the mixture was allowed to stand for 1.5 hours to be cooled to room temperature. The cooled solution was filtered, and was washed by filtration with about 1 L of distilled water. The residue after the filtration washing was dried at 120° C. for 8 hours or more to obtain Rh/HAP.

Production Example 8

Preparation of Comparative Mo/HAP:

Into a 100-ml eggplant flask containing 80 ml of distilled water, 25 ml of $(NH_4)_6Mo_7O_{24}·4H_2Oaq$ (40 mM) (Mo content: 1.0 mmol) was added dropwise. Then, the mixture was heated to 50° C. and was stirred for 3 hours. After stirring, the mixture was filtered and was washed by filtration with about 1 L of distilled water. The residue after the filtration washing was dried at 120° C. for 8 hours or more to obtain Mo/HAP.

Production Example 9

Preparation of Comparative Rh—Mo/$SiO_2$ (Catalyst Described in NPL 4):

Into a 100-ml flask containing 80 ml of distilled water, 0.4 mmol of $RhCl_3·3H_2O$ and 1.0 g of $SiO_2$(Fuji Silysia G-6) as a carrier were added, and were stirred at room temperature for 3 hours. After stirring, the solvent was removed with an evaporator, and then the resultant was dried at 120° C. for 8 hours or more. Rh/$SiO_2$ obtained after drying was added to a solution in which 0.4 mmol of $(NH_4)_6Mo_7O_{24}·4H_2O$ was dissolved in 70 ml of distilled water, and the mixture was stirred again at room temperature for 3 hours. Then, the solvent was removed with an evaporator, and the resultant was dried at 120° C. for 8 hours or more, and then the resultant was fired in the air in an electric furnace at 500° C. for 3 hours to obtain Rh—Mo/SiO$_2$.

Example 1

Hydrogenation Reaction:

Into an autoclave to be used for reaction, the catalyst obtained in Production Example 1 and 5 mL of 1,2-dimethoxyethane (DME) as a solvent were added, and the content was pressurized with hydrogen gas to 20 atm and was heated to 160° C. to perform a reduction treatment for 1 hours. Then, the product was subjected to a centrifuge (2000 rpm, 1 minute) and the supernatant was removed with a pipette. To the residue, 5 ml of DME was added and an ultrasonic treatment was applied for 1 minute. This washing step was repeated again and then, the resulting supernatant was removed, whereby a pre-reaction reduction treatment was applied.

0.05 g of the catalyst obtained in Production Example 1 having undergone the pre-reaction reduction treatment, 5 mL of 1,2-dimethoxyethane (DME) as a solvent, 0.5 mmol of N-acetylmorpholine as a substrate, and 0.1 g of Molecular Sieve 4 Å manufactured by Wako Pure Chemical Corporation were added into a 50 mL stainless steel autoclave, and a hydrogenation reaction was performed under conditions shown in Table 1. After the reaction, the yield was measured using gas chromatography. The result is shown in Table 1.

Note that the amounts of metal components in the catalysts of Entry 1 and Entry 2 were 2 mol % for Rh and 0.17 mol % for Mo based on the substrate. In addition, the amount of catalyst in Entry 3 was 0.3 g, and the amounts of metal components in the catalyst were 12 mol % for Rh and 1.02 mol % for Mo based on the substrate. The amounts of metal components supported in catalysts were determined by ICP emission spectral analysis (name of measurement apparatus: Optima 8300 manufactured by PerkinElmer).

TABLE 1

| Entry | Temperature [° C.] | Pressure [bar] | Time [h] | Selectivity [%] |
|---|---|---|---|---|
| 1 | 70 | 30 | 1 | 80 |
| 2 | 70 | 30 | 3 | 99 |
| 3 | 30 | 1 | 48 | 86 |

In Entry 2, the catalyst turnover number (TON) in terms of rhodium was 50. Although the temperature in Entry 3 was as low as 30° C., it was found that the catalyst of the present invention can promote a hydrogenation reaction into an amide compound at high efficiency.

Example 2

Hydrogenation Reaction:

For each substrate in Table 2, after Rh—Mo/HAP obtained in Production Example 1 was subjected to a pre-reaction reduction treatment in the same manner as in Example 1, 5 mL of DME as a solvent, hydrogen gas as a reductant, and Molecular Sieves 4 Å from Wako Pure Chemical Corporation were used to perform a hydrogenation reaction while appropriately varying the conditions. After the reaction, the conversion and selectivity to each substrate were measured using gas chromatography. The results are shown in Tables 2 and 3.

In Tables 2 and 3, in the reaction with no specific description, the amount of the catalyst was 0.1 g (Rh: 4 mol % based on the substrate, Mo: 0.34 mol % based on the substrate), and the amount of the substrate was 0.5 mmol, and the amount of DME as a solvent was 5 mL, and the amount of Molecular Sieves 4 Å from Wako Pure Chemical Corporation was 0.1 g.

In the reactions marked with (a), the amount of the catalyst was 0.3 g, the amount of the substrate was 0.25 mmol, the amount of Molecular Sieves 4 Å from Wako Pure Chemical Corporation was 0.2 g, and the other conditions were the same as in the reaction examples with no particular description.

In the reactions marked with (b), the amount of substrate was 0.25 mmol and the other conditions were the same as in the reaction examples with no particular description.

In the reactions marked with (c), the amount of the catalyst was 0.3 g, the amount of the substrate was 0.25 mmol, the amount of Molecular Sieves 4 Å from Wako Pure Chemical Corporation was 0.2 g, and the other conditions were the same as in the reaction examples with no particular description.

[Chem. 1]

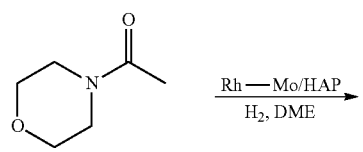

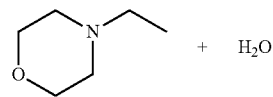

[Chem. 2]

TABLE 2

| Entry | Substrate | H₂ Pressure [bar] | Temperature [°C.] | Time [h] | Conversion [%] | Selectivity [%] |
|---|---|---|---|---|---|---|
| 1 | N-acetyl morpholine | 30 | 70 | 12 | >99 | >99 |
| 2 (a) | | 1 | 150 | 48 | >99 | >99 |
| 3 | N-acetyl piperidine | 30 | 70 | 12 | >99 | >99 |
| 4 (a) | | 1 | 150 | 48 | >99 | >99 |
| 5 | N-formyl piperidine | 30 | 70 | 24 | 98 | >99 |
| 6 (a) | | 1 | 150 | 48 | >99 | >99 |
| 7 | N-acetyl pyrrolidine | 30 | 70 | 12 | 98 | >99 |
| 8 (a) | | 1 | 150 | 48 | >99 | >99 |
| 9 | N-methyl pyrrolidinone | 30 | 70 | 48 | 92 | >99 |
| 10 (a) | | 1 | 150 | 48 | >99 | >99 |
| 11 (b) | N,N-dibutyl formamide | 30 | 70 | 48 | 79 | >99 |
| 12 (c) | | 1 | 120 | 72 | >99 | >99 |
| 13 | N,N-dimethyl octanamide | 30 | 70 | 12 | >99 | >99 |

TABLE 3

| Entry | Substrate | H2 Pressure [bar] | Temperature [°C.] | Time [h] | Conversion [%] | Selectivity [%] |
|---|---|---|---|---|---|---|
| 14 | morpholine cyclohexyl ketone amide | 30 | 70 | 12 | 90 | >99 |
| 15 (a) | | 1 | 150 | 72 | 90 | >99 |
| 16 (b) | piperidine cyclohexyl ketone amide | 30 | 70 | 48 | 91 | >99 |

TABLE 3-continued

| Entry | Substrate | H2 Pressure [bar] | Temperature [° C.] | Time [h] | Conversion [%] | Selectivity [%] |
|---|---|---|---|---|---|---|
| 17 (b) | azepan-2-one | 30 | 70 | 48 | 62 | >99 |
| 18 (a) | azepan-2-one | 1 | 150 | 48 | >99 | >99 |
| 19 (b) | N-phenyl tetradecanamide | 30 | 70 | 48 | 89 | >99 |
| 20 (b) | N-benzylacetamide | 30 | 70 | 48 | 84 | >99 |
| 21 (b) | 1-methylpyrrolidine-2,5-dione | 30 | 70 | 48 | >99 | >99 |
| 22 | hexahydroisoindole-1,3-dione | 30 | 150 | 24 | 90 | 78 |

It was found that Rh—Mo/HAP can promote a hydrogenation reaction of an amide compound with a high yield even under moderate conditions even when the substrate is varied, and the catalyst turnover number (TON) which represents the amount of the substrate hydrogenated per mole of Rh atom in the catalyst is also high. In particular, even at a quite low hydrogen gas pressure of 1 bar, the catalyst of the present invention surprisingly exhibits an excellent activity.

A hydrogenation reaction was performed in the same conditions as in Example 1 except that Rh, Pt, Pd, or Ru which are noble metal species was used in the catalyst of Production Examples 1 to 7 and 9 in an amount of 2 mol % based on the substrate, and Mo was used in the catalyst of Production Example 8 in an amount of 0.17 mol % based on the substrate, and $[Rh_6(CO)_{16} \cdot Mo(CO)_6]$ (the amount of Rh: 2 mol %, the amount of Mo: 12 mol %, based on the substrate) was used as a heterogenous catalyst as described in NPL 5, and the pressure and time were varied. For the Rh—Mo/HAP, the yield after the reaction was measured using gas chromatography. The results are shown in Table 4.

TABLE 4

| Catalyst | | Noble metal species Rh, Pt, Pd, Ru | Temperature [° C.] | Hydrogen pressure [bar] | Time [h] | Yield [%] |
|---|---|---|---|---|---|---|
| Production Example 1 | Rh—Mo/HAP | 2 mol % | 70 | 30 | 1 | 80 |
| Production Example 2 | Rh—Re/HAP | 2 mol % | 70 | 30 | 1 | 1 |
| Production Example 3 | Rh—V/HAP | 2 mol % | 70 | 30 | 1 | 31 |
| Production Example 4 | Pt—Mo/HAP | 2 mol % | 70 | 30 | 1 | 8 |
| Production Example 5 | Pd—Mo/HAP | 2 mol % | 70 | 30 | 1 | 2 |
| Production Example 6 | Ru—Mo/HAP | 2 mol % | 70 | 30 | 1 | 34 |
| Production Example 7 | Rh/HAP | 2 mol % | 70 | 30 | 1 | 0 |

TABLE 4-continued

| Catalyst | | Noble metal species Rh, Pt, Pd, Ru | Temperature [° C.] | Hydrogen pressure [bar] | Time [h] | Yield [%] |
|---|---|---|---|---|---|---|
| Production Example 8 | Mo/HAP | (Mo: 0.17 mol %) | 70 | 30 | 1 | 0 |
| Production Example 9 | Rh—Mo/SiO$_2$ | 2 mol % | 70 | 30 | 1 | 0 |
| | Rh$_6$(CO)$_{16}$·Mo(CO)$_6$ | 2 mol % | 70 | 30 | 1 | 0 |

It was found that Rh—Mo/HAP can promote a hydrogenation reaction of an amide compound with a high yield even under moderate conditions as compared not only to other catalysts of different metal species but also to a homogeneous catalyst.

Production Examples 10 to 14

Preparation of Rh—Mo/HAP:

Rh—Mo/HAP was obtained in the same manner as in Example 1 except for using (NH$_4$)$_6$Mo$_7$O$_{24}$·4H$_2$Oaq (40 mM) in an amount described in Table 4 in place of 25 ml of (NH$_4$)$_6$Mo$_7$O$_{24}$·4H$_2$Oaq (40 mM) (Mo content: 1.0 mmol) in Example 1.

TABLE 5

| | Rh [mmol/g] | Mo [mmol/g] |
|---|---|---|
| Production Example 10 | 0.2 | 1.0 |
| Production Example 11 | 0.2 | 0.6 |
| Production Example 12 | 0.2 | 0.4 |
| Production Example 13 | 0.2 | 0.3 |
| Production Example 14 | 0.2 | 0.1 |

Example 3

Hydrogenation Reaction:

Rh—Mo/HAP obtained in Production Examples 10 to 14 was subjected to a pre-reaction reduction treatment in the same manner as in Example 1, and 0.05 g of the resulting catalyst, 5 mL of 1,2-dimethoxyethane (DME) as a solvent, 0.5 mmol of N-acetylmorpholine as a substrate, and 0.1 g of Molecular Sieves 4 Å from Wako Pure Chemical Corporation were added to a 50-mL stainless steel autoclave, and were subjected to a hydrogenation reaction under the following conditions. After the reaction, the yield was measured using gas chromatography. The results are shown in Table 6.

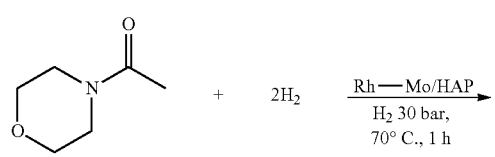

[Chem. 3]

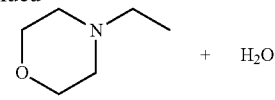

-continued

+ H$_2$O

TABLE 6

| | yield [%] |
|---|---|
| Production Example 10 | 81 |
| Production Example 11 | 45 |
| Production Example 12 | 42 |
| Production Example 13 | 40 |
| Production Example 14 | 31 |

It was found from the results that, as the amount of molybdenum in Rh—Mo/HAP increases, the yield increases.

Example 4

Durability of Catalyst:

A hydrogenation reaction was performed in the same conditions as in Entry 1 of Example 1 except for changing the reaction time to 12 hours. The catalyst after the reaction was filtered and reused, and this was repeated to examine the durability in the present invention. The conversion and yield were measured using gas chromatography. The results are shown in Table 7.

[Chem. 4]

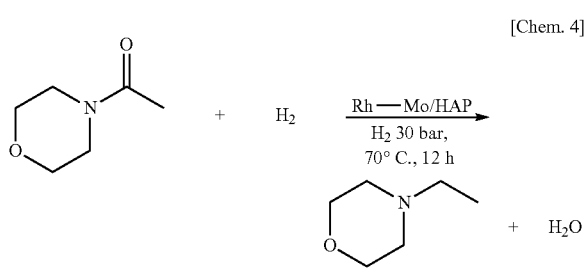

TABLE 7

| | Selectivity [%] |
|---|---|
| Reuse 1 | >99 |
| Reuse 2 | 96 |
| Reuse 3 | >99 |

TABLE 7-continued

|  | Selectivity [%] |
|---|---|
| Reuse 4 | >99 |
| Reuse 5 | >99 |
| Reuse 6 | >99 |
| Reuse 7 | 98 |
| Reuse 8 | 98 |
| Reuse 9 | 96 |
| Reuse 10 | 98 |

It was found from the results that the catalyst of the present invention is not decreased both in the conversion and yield even in reuse as much as 10 times and thus has excellent durability.

Example 5

Hydrogenation Reaction:

As shown in the following reaction formula, a hydrogenation reaction of an imide compound was performed using Rh—Mo/HAP obtained in Production Example 1 while changing the substrate in Example 1 to 0.3 mmol of the following imide (a compound having an amide bond), the amount of the catalyst to 0.3 g, the hydrogen pressure in the reaction to 50 bar, the temperature to 160° C., and the reaction time to 48 hours. After the reaction, the yield was measured using gas chromatography. Thus, an amine compound was able to be obtained at a yield of 60%.

[Chem. 5]

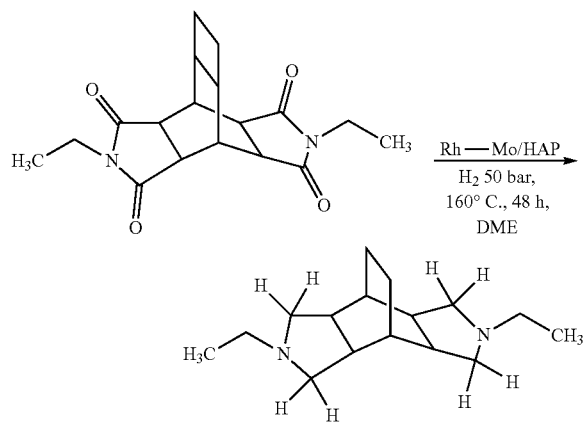

Example 6

Hydrogenation Reaction:

A hydrogenation reaction was performed with a reaction apparatus (ChemistPlaza CPP-2210 manufactured by Shibata Scientific Technology Ltd.) in the same manner as in Example 5 except for using 0.1 mmol of the substrate, 0.1 g of the catalyst, 10 ml of the solvent, and 0.2 g of the Molecular Sieves, and changing the reaction temperature to 60° C., the hydrogen pressure to 0.6 MPa, and the reaction time to 144 hours. The yield was 18%.

Example 7

Hydrogenation Reaction:

A reaction was performed in the same manner as in Example 6 except for using 15 ml of the solvent and 1.0 g of the Molecular Sieves. The yield was 41%. It was found from the results of Examples 6 and 7 that the yield was increased by putting an excess amount of molecular sieve relative to the amount of water produced from the substrate.

Test Example 1

Analysis of State of Rh and Mo in Catalyst:

In the catalyst of the present invention, the state of Rh and Mo was analyzed as follows. For Rh—Mo/HAP that had undergone hydrogen reduction before the reaction in Example 1, XAFS spectrum was measured. Then, the distance between Mo and an element in the vicinity of Mo was 2.66 Å (0.266 nm) as determined through the fast Fourier transform of the Mo—K edge EXAFS spectrum.

On the other hand, the Mo—Mo distance measured for Mo foil in the same manner was 2.73 Å (0.273 nm). In addition, the same measurement was performed for an intermetallic compound, such as a Mo—Rh alloy. Then, the Mo—Rh distance was 2.68 Å (0.268 nm).

It was found from this result that Mo having an interatomic distance that is closer to Mo—Rh rather than Mo—Mo exists in Mo in Rh—Mo/HAP of the present invention, which suggests that an alloyed Rh—Mo is contained.

Elemental mapping by an annular dark field-scanning transmission electron microscope (ADF-STEM) and an analysis by EDX also suggest that Rh and Mo that are alloyed are contained in the catalyst of the present invention as described above.

In addition, for the catalyst having undergone the hydrogen reduction treatment before the reaction in Example 1, the elemental distribution was examined by ADF-STEM and an analysis of the constituting elements at observation points was made by EDX. The results are shown in FIG. 1.

FIGS. 1(a), (b), (c), and (d) show the results of the ADF-STEM measurement. (a) is an image of Rh—Mo/HAP. (b) shows the elemental distribution of Ca and indicates that the carrier of the Rh—Mo/HAP is a homogenous HAP. (c) shows the elemental distribution of Rh and (d) shows the elemental distribution of Mo. It was found that Rh and Mo are both supported broadly over the carrier.

FIGS. 1(e) and (f) show analytical results of EDX. (e) shows a measurement point A (Point A) and a measurement point B (Point B) by EDX together with white points where Rh—Mo alloy is supposedly formed, and (f) shows the elements contained at the measurement point A (Point A) and the measurement point B (Point B).

It was found from the FIGS. 1(e) and (f) that Rh and Mo exist in the white particles (Point A) on the catalyst. It was also found that, in the gray background (Point B) on the catalyst, neither Rh nor Mo exists and P and Ca which are constitutional elements of HAP exist in the same manner as at Point A. The Y axis in FIG. 1(f) represents the X-ray intensity (count) and FIG. 1(f) shows a correlation thereof with the concentrations of elements contained. Based on the result for Point A in FIG. 1(f), the amounts of Rh and Mo at Point A almost coincide with the amounts of the Rh element and Mo element used in Production Example 1.

These results suggest that in Rh—Mo/HAP of the present invention, Rh and Mo are both broadly supported on HAP as a carrier and alloyed Rh—Mo may possibly be also contained.

Figure 2:
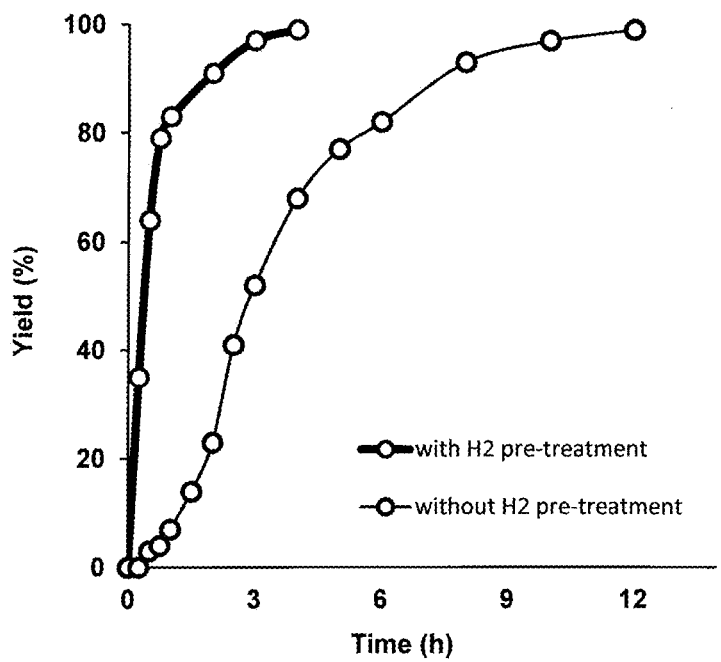
FIG. 2 It is a result of examination of the difference in the relation between the yield and the reaction time of the catalyst of the present invention depending on the presence or absence of the hydrogen reduction treatment.

Subsequently, the catalyst obtained in Production Example 1 was used to examine the effect of the reduction treatment of the catalyst. In Example 1, a mixture system of the catalyst in Production Example 1 and DME as a solvent was pressurized by hydrogen gas to 20 atm and was heated to 160° C. for 1 hours, thereby performing a reduction treatment before the reaction. In contrast, the same reaction as in Example 1 was performed using a catalyst without a reduction treatment. The result is shown in FIG. 2 together with the result of the catalyst with the reduction treatment. FIG. 2 shows results of measurement of yields of the reduced catalyst and the non-reduced catalyst over time.

As can be seen from FIG. 2, when the catalyst was subjected to the reduction treatment before reaction, the yield remarkably increased in a short period of time. In contrast, with the non-reduced catalyst, the increase in the yield was moderate. Such a catalyst that increases the yield in a short period of time can complete hydrogenation reaction in a short period of time and provides high efficiency in the energy required for reaction, and thus is an industrially advantageous catalyst. However, a non-reduced catalyst is expected to have a side-reaction suppressing effect and the like due to its moderate activity. Thus, depending on the embodiment of the present invention, use of a non-reduced catalyst may sometimes be desired.

Furthermore, XAFS of Rh and Mo was measured on a non-reduced catalyst, Rh foil, Mo foil, rhodium oxide, and $(NH_4)_6Mo_7O_{24}$ which was a raw material of Mo, in addition to a catalyst having undergone a reduction treatment. Spectral analysis was performed on X-ray absorption near edge structure (XANES). The result on Rh is shown in FIG. 3 and the result on Mo is shown in FIG. 4.

Figure 3:
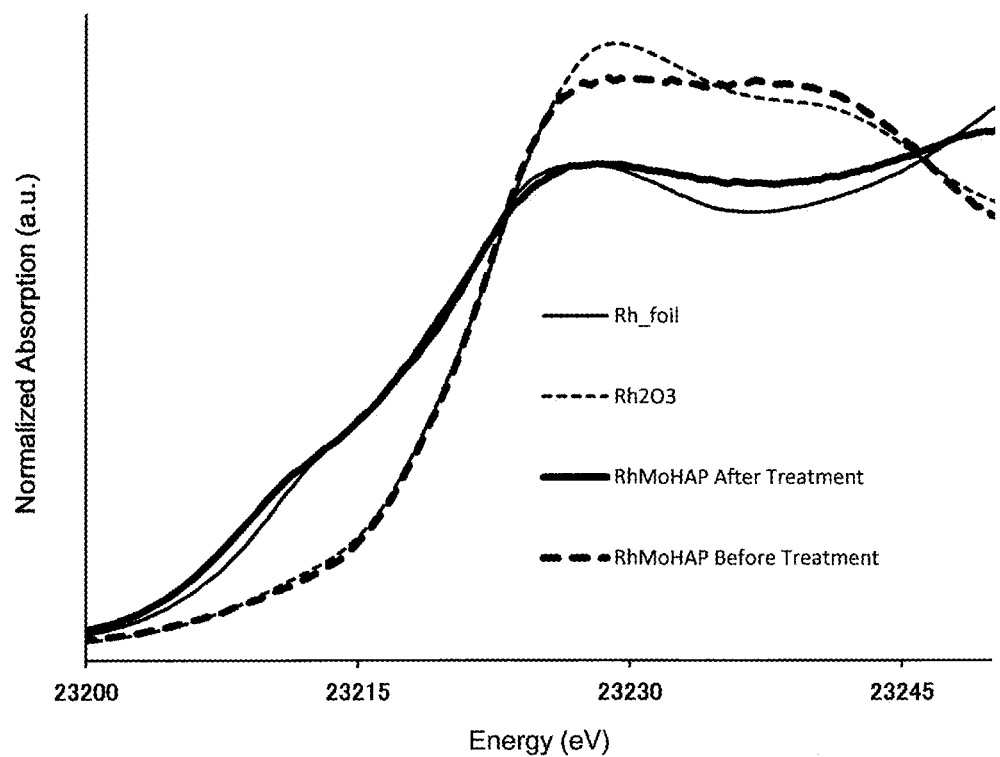
FIG. 3 It is a result of examination by XANES of the difference in Rh in the catalyst of the present invention depending on the presence and absence of the hydrogen reduction treatment.
Figure 4:
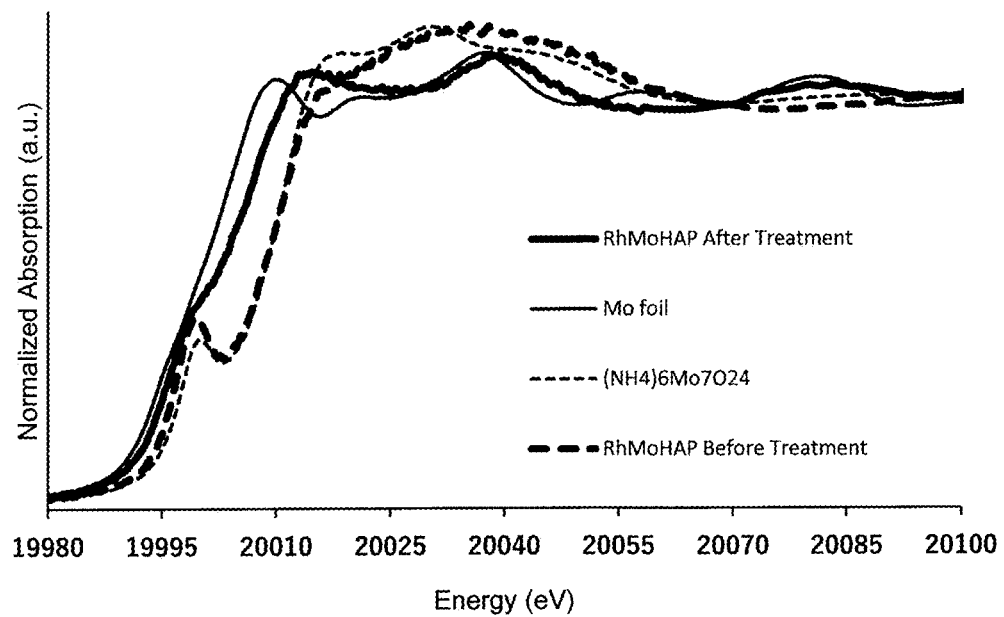
FIG. 4 It is a result of examination by XANES of the difference in Mo in the catalyst of the present invention depending on the presence and absence of the hydrogen reduction treatment.

As can be seen from FIGS. 3 and 4, as a result of the hydrogen reduction of the catalyst of the present invention, the shapes of the lines for Rh and Mo are similar to Rh foil and Mo foil, respectively, which suggests that the reduced Rh—Mo/HAP of the present invention is in the metallic state for both of Rh and Mo. On the other hand, it is suggested that in the Rh—Mo/HAP of the present invention before the reduction treatment, Rh and Mo mostly exist in the oxide state.

INDUSTRIAL APPLICABILITY

The catalyst of the present invention is useful for safely producing amino compounds which are useful in medicine, agrochemical, or other various industrial fields under moderate conditions. In addition, the catalyst of the present invention can be produced in an inexpensive and safe manner.

The invention claimed is:

1. A catalyst for amide compound hydrogenation, the catalyst comprising:
   hydroxyapatite, and
   rhodium and molybdenum that are supported on the hydroxyapatite,
   wherein a molar ratio of rhodium to molybdenum is 1:0.05-0.2; and
   wherein an amount of molybdenum supported is between 0.01 mmol/g and 0.03 mmol/g.

2. The catalyst for amide compound hydrogenation according to claim 1, wherein the amide compound is a secondary or higher amide compound or an amide compound having an aromatic substituent.

* * * * *